US006133231A

United States Patent [19]
Ferrara et al.

[11] Patent Number: 6,133,231
[45] Date of Patent: Oct. 17, 2000

[54] ANGIOGENESIS USING HEPATOCYTE GROWTH FACTOR

[75] Inventors: Napoleone Ferrara, San Francisco, Calif.; Jeffrey M. Isner, Weston, Mass.; Ralph H. Schwall, Pacifica, Calif.

[73] Assignees: Genentech, Inc., South San Francisco, Calif.; St. Elizabeth's Medical Center of Boston, Inc., Boston, Mass.

[21] Appl. No.: 09/086,498

[22] Filed: May 22, 1998

Related U.S. Application Data

[63] Continuation of application No. 08/726,110, Oct. 4, 1996, abandoned.
[60] Provisional application No. 60/004,816, Oct. 5, 1995.
[51] Int. Cl.[7] .................................................. A61K 38/18
[52] U.S. Cl. .................................................. 514/2; 514/12
[58] Field of Search ........................................... 514/2, 12

[56] References Cited

U.S. PATENT DOCUMENTS

| | | | |
|---|---|---|---|
| 5,227,158 | 7/1993 | Jardieu | 424/85.5 |
| 5,316,921 | 5/1994 | Godowski et al. | 435/69.4 |
| 5,328,837 | 7/1994 | Godowski et al. | 435/69.4 |
| 5,401,832 | 3/1995 | Linemeyer et al. | 530/399 |
| 5,652,225 | 7/1997 | Isner | 514/44 |

FOREIGN PATENT DOCUMENTS

| | | |
|---|---|---|
| 7-304796 | 11/1995 | Japan . |
| 8-295634 | 11/1996 | Japan . |
| WO 92/13097 | 8/1992 | WIPO . |
| WO 92/20792 | 11/1992 | WIPO . |
| WO 93/15754 | 8/1993 | WIPO . |

OTHER PUBLICATIONS

Bauters et al. "Site–Specific Therapeutic Angiogenesis After Systemic Administration of Vascular Endothelial Growth Factor", J. Vasc. Surg. 21(2), pp. 314–325, Feb. 1995.

*Remington's Pharmaceutical Sciences,* Oslo et al., eds., 16th edition, Mack Publishing Co. (1980).

Asami et al., "Purification and Characterization of Hepatocyte Growth Factor from Injured Liver of Carbon Tetrachloride–Treated Rats" *J. Biochem.* 109:8–13 (1991).

Bottaro et al., "Identification of the Hepatocyte Growth Factor Receptor as the c–met Proto–Oncogene Product" *Science* 251:802–804 (Feb. 15, 1991).

Bowman et al. *Textbook of Pharmacology,* 2nd Edition edition, Oxford:Blackwell Scientific pp. 40.16–40.17 (1980).

Bussolino et al., "Hepatocyte Growth Factor is a Potent Angiogenic Factor Which Stimulates Endothelial Cell Motility and Growth" *Journal of Cell Biology* 119(3):629–641 (Nov. 1992).

Chan et al., "Identification of a Competitive HGF Antagonist Encoded by an Alternative Transcript" *Science* 254:1382–1385 (1991).

Chan et al., "Isoforms of Human HGF and Their Biological Activities" *Hepatocyte Growth Factor–Scatter Factor (HGF–SF) and the C–Met Receptor,* I.D. Goldberg and E.M. Rosen eds., Basel:Birkhauser Verlag pp. 67–79 (1993).

Comoglio, "Structure, Biosynthesis and Biochemical Properties of the HGF Receptor in Normal and Malignant Cells" *Hepatocyte Growth Factor–Scatter Factor (HGF–SF) and the C–Met Receptor,* I.D. Goldberg and E.M. Rosen eds., Basel:Birkhauser Verlag pp. 131–165 (1993).

Cristiani et al., "Inhibition of Hepatocyte Growth Factor in vitro biological activity by sulfonated distamycin A derivatives [D" *Proc. Ann. Meet. Am. Assoc. Can. Res.* (abstract 2267) 35:380 (1994).

Di Renzo et al., "Selective Expression of the Met/HGF Receptor in Human Central Nervous System Microglia" *Oncogene* 8:219–222 (1993).

Esch et al., "Primary structure of bovine pituitary basic fibroblast growth factor (FGF) and Comparison with the amino–terminal sequence of bovine brain Acidic FGF" *Proc. Natl. Acad. Sci. USA* 82:6507–6511 (1985).

Ferrara et al., "Purification and Cloning of Vascular Endothelial Growth Factor Secreted by Pituitary Folliculostellate Cells" *Methods Enzym.* 198:391–405 (1991).

Giordano et al., "Transfer of Motogenic and Invasive Response to Scatter Factor/Hepatocyte Growth Factor by Transfection of Human met Protooncogene" *Proc. Natl. Acad. Sci. USA* 90:649–653 (Jan. 1993).

Gohda et al., "Purification and Partial Characterization of Hepatocyte Growth Factor from Plasma of a Patient with Fulminant Hepatic Failure" *J. Clin. Invest.* 81:414–419 (1988).

Grant et al., "Scatter Factor Induces Blood Vessel Formation In Vivo" *Proc. Natl. Acad. Sci. USA* 90:1937–1941 (1993).

Han et al., "Characterization of the DNF15S2 Locus on Human Chromosome 3: Identification of a Gene Coding for Four Kringle Domains with Homology to Hepatocyte Growth Factor" *Biochemistry* 30:9768–9780 (1991).

Hartmann et al., "A Functional Domain in the Heavy Chain of Scatter Factor/Hepatocyte Growth Factor Binds the c–Met Receptor and Induces Cell Dissociation but Not Mitogenesis" *Proc. Natl. Acad. Sci. USA* 89:11574–11578 (Dec. 1992).

Hyink and Abrahamson, "Origin of the Glomerular Vasculature in the Developing Kidney" *Seminars in Nephrology* 15(4):300–314 (Jul. 1995).

Igawa et al., "Hepatocyte Growth Factor is a Potent Mitogen for Cultured Rabbit Renal Tubular Epithelial Cells" *Biochem. & Biophys. Res. Comm.* 174(2):831–838 (Jan. 31, 1991).

(List continued on next page.)

*Primary Examiner*—Jon P. Weber
*Attorney, Agent, or Firm*—Piper, Marbury, Rudnick & Wolfe, LLP; Steven B. Kelber

[57] ABSTRACT

Methods for enhancing angiogenesis in a mammal using hepatocyte growth factor ("HGF") are provided. In the methods, HGF can be administered to mammals suffering from, for instance, vascular insufficiency or arterial occlusive disease. Articles of manufacture and kits containing HGF are also provided.

7 Claims, No Drawings

OTHER PUBLICATIONS

Lindroos et al., "Hepatocyte Growth Factor (Hepatopoietin A) Rapidly Increases in Plasma before DNA Synthesis and Liver Regeneration Stimulated by Partial Hepatectomy and Carbon Tetrachloride Administration" *Hepatology* 13(4):743–750 (1991).

Lokker et al., "Generation and Characterization of a Competitive Antagonist of Human Hepatocyte Growth Factor, HGF/NK1" *Journal of Biological Chemistry* 268(23):17145–17150 (Aug. 15, 1993).

Lokker et al., "Structure–Function Analysis of Hepatocyte Growth Factor: Identification of Variants that Lack Mitogenic Activity Yet Retain High Affinity Receptor Binding" *EMBO Journal* 11(7):2503–2510 (1992).

Matsumoto et al., "Deletion of Kringle Domains or the N–Terminal Hairpin Structure in Hepatocyte Growth Factor Results in Marked Decreases in Related Biological Activities" *Biochem. & Biophys. Res. Comm.* 181(2):691–699 (Dec. 16, 1991).

Matsumoto et al., "Hepatocyte Growth Factor is a Potent Stimulator of Human Melanocyte DNA Synthesis and Growth" *Biochem. & Biophys. Res. Comm.* 176(1):45–51 (Apr. 15, 1991).

Mayer et al., "Chapter 1; Introduction; the dynamics of drug absorption, distribution and elimination" *The Pharmacological Basis of Therapeutics,* Goodman et al., New York-:MacMillan Publishing Co., Inc. pp. 7–8 (1980).

Michalopoulos et al., "Control of Hepatocyte Replication by Two Serum Factors" *Cancer Research* 44:4414–4419 (Oct. 1984).

Miyazawa et al., "An Alternatively Processed mRNA Generated from Human Hepatocyte Growth Factor Gene" *European Journal of Biochemistry* 197:15–22 (1991).

Miyazawa et al., "Molecular Cloning and Sequence Analysis of cDNA for Human Hepatocyte Growth Factor" *Biochem. & Biophys. Res. Comm.* 163(2):967–973 (Sep. 15, 1989).

Montesano et al., "Identification of a Fibroblast–Derived Epithelial Morphogen as Hepatocyte Growth Factor" *Cell* 67:901–908 (Nov. 29, 1991).

Morimoto et al., "Hepatocyte Growth Factor Modulates Migration and Proliferation of Human Microvascular Endothelial Cells in Culture" *Biochem. & Biophys. Res. Comm.* 179:1042–1049 (1991).

Nagy et al., "Relationship of C–met receptor expression with clinical and pathological variables in breast cancer" *J. Pathol.* (abstract) 173((supplement)):160A (1994).

Naidu et al., "Role of scatter factor in the pathogenesis of AIDS–related Kaposi sarcoma" *Proc. Natl. Acad. Sci. USA* 91:5281–5285 (1994).

Naka et al., "Activation of Hepatocyte Growth Factor by Proteolytic Conversion of a Single Chain Form to a Heterodimer" *The Journal of Biological Chemistry* 267(28):20114–20119 (1992).

Nakamura et al., "Molecular Cloning and Expression of Human Hepatocyte Growth Factor" *Nature* 342:440–443 (Nov. 23, 1989).

Nakamura et al., "Partial Purification and Characterization of Hepatocyte Growth Factor from Serum of Hepatectomized Rats" *Biochem. & Biophys. Res. Comm.* 122:1450–1459 (Aug. 16, 1984).

Nakamura et al., "Purification and Characterization of a Growth Factor from Rat Platelets for Mature Parenchymal Hepatocytes in Primary Cultures" *Proc. Natl. Acad. Sci, USA* 83:6489–6493 (1986).

Nakamura et al., "Purification and Subunit Structure of Hepatocyte Growth Factor from Rat Platelets" *FEBS Letters* 224(2):311–316 (Nov. 1987).

Naldini et al., "Hepatocyte Growth Factor (HGF) Stimulates the Tyrosine Kinase Activity of the Receptor Encoded by the Proto–Oncogene c–MET" *Oncogene* 6:501–504 (1991).

Naldini et al., "Scatter Factor and Hepatocyte Growth Factor are Indistinguishable Ligands for the MET Receptor" *EMBO Journal* 10(10):2867–2878 (1991).

Okajima et al., "Primary Structure of Rat Hepatocyte Growth Factor and Induction of Its mRNA During Liver Regeneration Following Hepatic Injury" *European Journal of Biochemistry* 193:375–381 (1990).

Park et al., "Sequence of MET Protooncogene cDNA has Features Characteristic of the Tyrosine Kinase Family of Growth–Factor Receptors" *Proc. Natl. Acad. Sci. USA* 84:6379–6383 (1987).

Ponzetto et al., "c–met is Amplified But Not Mutated in a Cell Line with an Activated met Tyrosine Kinase" *Oncogene* 6:553–559 (1991).

Prat et al., "C–Terminal Truncated Forms of Met, the Hepatocyte Growth Factor Receptor" *Molecular & Cellular Biology* 11(12):5954–5962 (1991).

Rodrigues et al., "Alternative Splicing Generates Isoforms of the met Receptor Tyrosine Kinase Which Undergo Differential Processing" *Molecular & Cellular Biology* 11(6):2962–2970 (1991).

Rosen and Goldberg, "Scatter Factor and Angiogenesis" *Advances in Cancer Research* 67:257–279 (1995).

Rosen et al., "The interaction of HGF–SF with other cytokines in tumor invasion and angiogenesis" *Hepocyte Growth Factor–Scatter Factor (HGF–SF) and the C–met Receptor,* Goldberg et al., Basel:Birkhauser Verlag pp. 301–310 (1993).

Rosen et al., "Scatter Factor (hepatocyte growth factor) Is a Potent Angiogenesis Factor In Vivo" *Symposia of the Society for Experimental Biology* (Abstract Only) 47:227–234 (1993).

Rubin et al., "A Broad–Spectrum Human Lung Fibroblast–Derived Mitogen is a Variant of Hepatocyte Growth Factor" *Proc. Natl. Acad Sci, USA* 88:415–419 (1991).

Russell et al., "Partial Characterization of a Hepatocyte Growth Factor From Rat Platelets" *J. Cellular Physiology* 119:183–192 (1984).

Seki et al., "Isolation and Expression of cDNA for Different Forms of Hepatocyte Growth Factor from Human Leukocyte" *Biochem. and Biophys. Res. Commun.* 172(1):321–327 (Oct. 15, 1990).

Silvagno et al., "In Vivo Activation of Met Tyrosine Kinase by Heterodimeric Hepatocyte Growth Factor Molecule Promotes Angiogenesis" *Arterioscler. Thromb. Vasc. Biol.* 15:1857–1865 (1995).

Stoker et al., "Scatter Factor is a Fibroblast–Derived Modulator of Epithelial Cell Mobility" *Nature* 327:239–242 (May 21, 1987).

Takeshita et al., "Therapeutic angiogenesis. A single intraarterial bolus of vascular endothelial growth factor augments revascularization in a rabbit ischemic hind limb model" *J. Clin. Invest.* 93(2):662–670 (Feb. 1994).

Taniguchi et al., "Rapid induction of hepatocyte growth factor by heparin" *Lancet* (letter) 344:470 (1994).

Tashiro et al., "Deduced Primary Structure of Rat Hepatocyte Growth Factor and Expression of the mRNA in Rat Tissues" *Proc. Natl. Acad. Sci. USA* 87:3200–3204 (1990).

Van Belle et al., "Scatter factor stimulates angiogenesis in a robbit model of Hindlimb Ischemia" *Circulation* (abstract No. 3598) 92(8, supplement):1748 (1995).

Weidner et al., "Scatter Factor: Molecular Characteristics and Effect on the Invasiveness of Epithelial Cells" *Journal of Cell Biology* 111:2097–2108 (Nov. 1990).

Yoshinaga et al., "Human lung cancer line producing hepatocyte growth factor/scatter factor" *Jpn. J. Cancer Res.* 83(12):1257–1261 (1992).

Yoshinaga et al., "Immunohistochemical detection of hepatocyte growth factor/scatter factor in human cancerous and inflammatory lesions of various organs." *Jpn. J. Cancer Res.* 84(11):1150–1158 (1993).

Zarnegar et al., "Expression of HGF–SF in normal and malignant human tissues" *Hepatocyte Growth Factor–Scatter Factor (HGF–SF) and the C–Met Receptor,* Golfbert et al., Basel:Birkhauser Verlag pp. 181–199 (1993).

ANGIOGENESIS USING HEPATOCYTE GROWTH FACTOR

This is a continuation application claiming priority to application Ser. No. 08/726,110, filed Oct. 4, 1996 now abandoned provisional application, the entire disclosure of which is hereby incorporated by reference.

RELATED APPLICATIONS

This application is a non-provisional application filed under 37 CFR 1.53(b)(1) and 35 USC 111(a), claiming priority under 35 USC 119(e) to provisional application number 60/004,816 filed Oct. 5, 1995, the contents of which are incorporated herein by reference.

FIELD OF THE INVENTION

The invention relates generally to methods and compositions which can be employed for enhancing angiogenesis in mammals.

BACKGROUND OF THE INVENTION

Hepatocyte growth factor ("HGF") functions as a growth factor for particular tissues and cell types. HGF was identified initially as a mitogen for hepatocytes [Michalopoulos et al., Cancer Res., 44:4414–4419 (1984); Russel et al., J. Cell. Physiol., 119:183–192 (1984); Nakamura et al., Biochem. Biophys. Res. Comm., 122:1450–1459 (1984)]. Nakamura et al., supra, reported the purification of HGF from the serum of partially hepatectomized rats. Subsequently, HGF was purified from rat platelets, and its subunit structure was determined [Nakamura et al., Proc. Natl. Acad. Sci. USA, 83:6489–6493 (1986); Nakamura et al., FEBS Letters, 224:311–316 (1987)]. The purification of human HGF ("huHGF") from human plasma was first described by Gohda et al., J. Clin. Invest., 81:414–419 (1988).

Both rat HGF and huHGF have been molecularly cloned, including the cloning and sequencing of a naturally occurring variant lacking 5 amino acids designated "delta5 HGF" [Miyazawa et al., Biochem. Biophys. Res. Comm., 163:967–973 (1989); Nakamura et al., Nature, 342:440–443 (1989); Seki et al, Biochem. Biophys. Res. Commun., 172:321–327 (1990); Tashiro et al., Proc. Natl. Acad. Sci. USA, 87:3200–3204 (1990); Okajima et al., Eur. J. Biochem., 193:375–381 (1990)].

The mature form of huHGF, corresponding to the major form purified from human serum, is a disulfide linked heterodimer derived by proteolytic cleavage of the human pro-hormone between amino acids R494 and V495. This cleavage process generates a molecule composed of an α-subunit of 440 amino acids ($M_r$ 69 kDa) and a β-subunit of 234 amino acids ($M_r$ 34 kDa). The nucleotide sequence of the huHGF cDNA reveals that both the α- and the β-chains are contained in a single open reading frame coding for a pre-pro precursor protein. In the predicted primary structure of mature huHGF, an interchain S—S bridge is formed between Cys 487 of the α-chain and Cys 604 in the β-chain [see Nakamura et al., Nature, supra]. The N-terminus of the α-chain is preceded by 54 amino acids, starting with a methionine group. This segment includes a characteristic hydrophobic leader (signal) sequence of 31 residues and the prosequence. The α-chain starts at amino acid (aa) 55, and contains four kringle domains. The kringle 1 domain extends from about aa 128 to about aa 206, the kringle 2 domain is between about aa 211 and about aa 288, the kringle 3 domain is defined as extending from about aa 303 to about aa 383, and the kringle 4 domain extends from about aa 391 to about aa 464 of the α-chain.

The definition of the various kringle domains is based on their homology with kringle-like domains of other proteins (such as prothrombin and plasminogen), therefore, the above limits are only approximate. To date, the function of these kringles has not been determined. The β-chain of huHGF shows high homology to the catalytic domain of serine proteases (38% homology to the plasminogen serine protease domain). However, two of the three residues which form the catalytic triad of serine proteases are not conserved in huHGF. Therefore, despite its serine protease-like domain, huHGF appears to have no proteolytic activity, and the precise role of the β-chain remains unknown. HGF contains four putative glycosylation sites, which are located at positions 294 and 402 of the α-chain and at positions 566 and 653 of the β-chain.

In a portion of cDNA isolated from human leukocytes, in-frame deletion of 15 base pairs was observed. Transient expression of the cDNA sequence in COS-1 cells revealed that the encoded HGF molecule (delta5 HGF) lacking 5 amino acids in the kringle 1 domain was fully functional [Seki et al., supra].

A naturally occurring huHGF variant has been identified which corresponds to an alternative spliced form of the huHGF transcript containing the coding sequences for the N-terminal finger and first two kringle domains of mature huHGF [Chan et al., Science, 254:1382–1385 (1991); Miyazawa et al., Eur. J. Biochem., 197:15–22 (1991)]. This variant, designated HGF/NK2, has been proposed to be a competitive antagonist of mature huHGF.

Comparisons of the amino acid sequence of rat HGF with that of huHGF have revealed that the two sequences are highly conserved and have the same characteristic structural features. The length of the four kringle domains in rat HGF is exactly the same as in huHGF. Furthermore, the cysteine residues are located in exactly the same positions, an indication of similar three-dimensional structures [Okajima et al., supra; Tashiro et al., supra].

HGF and HGF variants are described further in U.S. Pat. Nos. 5,227,158, 5,316,921, and 5,328,837.

The HGF receptor has been identified as the product of the c-Met proto-oncogene [Bottaro et al., Science, 251:802–804 (1991); Naldini et al., Oncogene, 6:501–504 (1991); WO 92/13097 published Aug. 6, 1992; WO 93/15754 published Aug. 19, 1993]. The receptor is usually referred to as "c-Met" or "$p190^{MET}$" and typically comprises, in its native form, a 190-kDa heterodimeric (a disulfide-linked 50-kDa α-chain and a 145-kDa β-chain) membrane-spanning tyrosine kinase protein [Park et al., Proc. Natl. Acad. Sci. USA, 84:6379–6383 (1987)]. Several truncated forms of the c-Met receptor have also been described [WO 92/20792; Prat et al., Mol. Cell. Biol., 11:5954–5962 (1991)].

The binding activity of HGF to its receptor is believed to be conveyed by a functional domain located in the N-terminal portion of the HGF molecule, including the first two kringles [Matsumoto et al., Biochem. Biophys. Res. Commun., 181:691–699 (1991); Hartmann et al., Proc. Natl. Acad. Sci., 89:11574–11578 (1992); Lokker et al., EMBO J., 11:2503–2510 (1992); Lokker and Godowski, J. Biol. Chem., 268:17145–17150 (1991)]. The c-Met protein becomes phosphorylated on tyrosine residues of the 145-kDa β-subunit upon HGF binding.

Various biological activities have been described for HGF and its receptor [see, generally, Chan et al., Hepatocyte Growth Factor-Scatter Factor (HGF-SF) and the C-Met

*Receptor*, Goldberg and Rosen, eds., Birkhauser Verlag-Basel (1993), pp. 67–79]. It has been observed that levels of HGF increase in the plasma of patients with hepatic failure [Gohda et al., supra] and in the plasma [Lindroos et al., *Hepatol.*, 13:734–750 (1991)] or serum [Asami et al., *J. Biochem.*, 109:8–13 (1991)] of animals with experimentally induced liver damage. The kinetics of this response are usually rapid, and precedes the first round of DNA synthesis during liver regeneration. HGF has also been shown to be a mitogen for certain cell types, including melanocytes, renal tubular cells, keratinocytes, certain endothelial cells and cells of epithelial origin [Matsumoto et al., *Biochem. Biophys. Res. Commun.*, 176:45–51 (1991); Igawa et al., *Biochem. Biophys. Res. Commun.*, 174:831–838 (1991); Han et al., *Biochem.*, 30:9768–9780 (1991); Rubin et al., *Proc. Natl. Acad. Sci. USA*, 88:415–419 (1991)]. Both HGF and the c-Met protooncogene have been postulated to play a role in microglial reactions to CNS injuries [DiRenzo et al., *Oncogene*, 8:219–222 (1993)].

HGF can also act as a "scatter factor", an activity that promotes the dissociation of epithelial and vascular endothelial cells in vitro [Stoker et al., *Nature*, 327:239–242 (1987); Weidner et al., *J. Cell Biol.*, 111:2097–2108 (1990); Naldini et al., *EMBO J.*, 10:2867–2878 (1991); Giordano et al., *Proc. Natl. Acad. Sci. USA*, 90:649–653 (1993)]. Moreover, HGF has recently been described as an epithelial morphogen [Montesano et al., Cell, 67:901–908 (1991)]. Therefore, HGF has been postulated to be important in tumor invasion [Comoglio, *Hepatocyte Growth Factor-Scatter Factor (HGF-SF) and the C-Met Receptor*, Goldberg and Rosen, eds., Birkhauser Verlag-Basel (1993), pp. 131–165].

Therapeutic options for patients with vascular disease, particularly vascular obstructive disease, are sometimes limited. As Takeshita et al., *J. Clin. Invest.*, 93:662–670 (1994), point out, such patients are often refractory to conservative measures and typically unresponsive to drug therapy. When vascular obstruction is lengthy and/or widespread, nonsurgical revascularization may not be feasible. Id. Surgical therapy, consisting of arterial bypass and/or amputation, may be complicated by a variable morbidity and mortality, and is often dependent for its efficacy upon short- and long-term patency of the conduit used. Id. Therapeutic angiogenesis thus constitutes an alternative treatment strategy for such patients.

SUMMARY OF THE INVENTION

The invention provides methods for enhancing angiogenesis in a mammal comprising administering to the mammal an effective amount of HGF. The HGF alone may be administered to the mammal, or alternatively, may be administered to the mammal in combination with other therapies and/or pharmacologic agents.

The invention also provides articles of manufacture and kits which contain HGF.

Although not being bound by any particular theory, it is presently believed that the HGF can be used to stimulate or enhance angiogenic activity in patients suffering from vascular insufficiency or limb ischemia secondary to arterial occlusive disease.

DETAILED DESCRIPTION OF THE INVENTION

I. Definitions

As used herein, the terms "hepatocyte growth factor" and "HGF" refer to a growth factor typically having a structure with six domains (finger, Kringle 1, Kringle 2, Kringle 3, Kringle 4 and serine protease domains). Fragments of HGF constitute HGF with fewer domains and variants of HGF may have some of the domains of HGF repeated; both are included if they still retain their respective ability to bind a HGF receptor. The terms "hepatocyte growth factor" and "HGF" include hepatocyte growth factor from humans ("huHGF") and any non-human mammalian species, and in particular rat HGF. The terms as used herein include mature, pre, pre-pro, and pro forms, purified from a natural source, chemically synthesized or recombinantly produced. Human HGF is encoded by the cDNA sequence published by Miyazawa et al., 1989, supra, or Nakamura et al., 1989, supra. The sequences reported by Miyazawa et al. and Nakamura et al. differ in 14 amino acids. The reason for the differences is not entirely clear; polymorphism or cloning artifacts are among the possibilities. Both sequences are specifically encompassed by the foregoing terms. It will be understood that natural allelic variations exist and can occur among individuals, as demonstrated by one or more amino acid differences in the amino acid sequence of each individual. The HGF of the invention preferably has at least about 80% sequence identity, more preferably at least about 90% sequence identity, and even more preferably, at least about 95% sequence identity with a native mammalian HGF. The terms "hepatocyte growth factor" and "HGF" specifically include the delta5 huHGF as disclosed by Seki et al., supra.

The terms "HGF receptor" and "c-Met" when used herein refer to a cellular receptor for HGF, which typically includes an extracellular domain, a transmembrane domain and an intracellular domain, as well as variants and fragments thereof which retain the ability to bind HGF. The terms "HGF receptor" and "c-Met" include the polypeptide molecule that comprises the full-length, native amino acid sequence encoded by the gene variously known as $p190^{MET}$. The present definition specifically encompasses soluble forms of HGF receptor, and HGF receptor from natural sources, synthetically produced in vitro or obtained by genetic manipulation including methods of recombinant DNA technology. The HGF receptor variants or fragments preferably share at least about 65% sequence homology, and more preferably at least about 75% sequence homology with any domain of the human c-Met amino acid sequence published in Rodrigues et al., *Mol. Cell. Biol.*, 11:2962–2970 (1991); Park et al., *Proc. Natl. Acad. Sci.*, 84:6379–6383 (1987); or Ponzetto et al., *Oncogene*, 6:553–559 (1991).

The term "angiogenesis" is used herein in a broad sense and refers to the production or development of blood vessels.

The terms "treating," "treatment," and "therapy" as used herein refer to curative therapy, prophylactic therapy, and preventative therapy.

The term "mammal" as used herein refers to any mammal classified as a mammal, including humans, cows, horses, dogs and cats. In a preferred embodiment of the invention, the mammal is a human.

II. Compositions and Methods of the Invention

The present invention provides methods for enhancing angiogenesis using hepatocyte growth factor, referred to hereinafter as "HGF". The HGF useful in the practice of the present invention can be prepared in a number of ways. For instance, the HGF can be prepared using an isolated or purified form of HGF. Methods of isolating and purifying HGF from natural sources are known in the art. Such isolation and purification methods can be employed for obtaining HGF from serum or plasma. Alternatively, HGF can be chemically synthesized and prepared using recombinant DNA techniques known in the art and described in further detail in the Example below.

The HGF may be from human or any non-human species. For instance, a mammal may have administered HGF from a different mammalian species (e.g., rats can be treated with human HGF). Preferably, however, the mammal is treated with homologous HGF (e.g., humans are treated with human HGF) to avoid potential immune reactions to the HGF. The HGF is typically administered to a mammal diagnosed as having some form of vascular insufficiency or vascular disease. It is of course contemplated that the methods of the invention can be employed in combination with other therapeutic techniques such as surgery.

The HGF is preferably administered to the mammal in a pharmaceutically-acceptable carrier. Suitable carriers and their formulations are described in *Remington's Pharmaceutical Sciences*, 16th ed., 1980, Mack Publishing Co., edited by Oslo et al. Typically, an appropriate amount of a pharmaceutically-acceptable salt is used in the formulation to render the formulation isotonic. Examples of the pharmaceutically-acceptable carrier include liquids such as saline, Ringer's solution and dextrose solution. The pH of the solution is preferably from about 5 to about 8, and more preferably from about 7 to about 7.5. The formulation may also comprise a lyophilized powder. Further carriers include sustained release preparations such as semipermeable matrices of solid hydrophobic polymers, which matrices are in the form of shaped articles, e.g., films, liposomes or microparticles. It will be apparent to those persons skilled in the art that certain carriers may be more preferable depending upon, for instance, the route of administration and concentration of HGF being administered.

The HGF can be administered to the mammal by injection (e.g. intravenous, intraarterial, intraperitoneal, subcutaneous, intramuscular), or by other methods such as infusion that ensure its delivery to the bloodstream in an effective form. Optionally, the HGF may be administered by direct intraarterial administration upstream from an occluded artery to optimize concentration and activity of HGF in the local circulation of an affected limb.

Effective dosages and schedules for administering the HGF may be determined empirically, and making such determinations is within the skill in the art. Those skilled in the art will understand that the dosage of HGF that must be administered will vary depending on, for example, the mammal which will receive the HGF, the route of administration, the particular type of HGF used and other drugs being administered to the mammal. A typical daily dosage of the HGF used alone might range from about 1 $\mu$g/kg to up to 100 mg/kg of body weight or more per day, depending on the factors mentioned above.

HGF may also be administered along with other pharmacologic agents used to treat the conditions associated with vascular disease such as vascular endothelial growth factor ("VEGF"). The HGF may be administered sequentially or concurrently with the one or more other pharmacologic agents. The amounts of HGF and pharmacologic agent depend, for example, on what type of drugs are used, the specific condition being treated, and the scheduling and routes of administration.

Following administration of HGF to the mammal, the mammal's physiological condition can be monitored in various ways well known to the skilled practitioner.

In another embodiment of the invention, there are provided articles of manufacture and kits containing materials useful for enhancing angiogenesis. The article of manufacture comprises a container with a label. Suitable containers include, for example, bottles, vials, and test tubes. The containers may be formed from a variety of materials such as glass or plastic. The container holds a composition which is effective for enhancing angiogenesis. The active agent in the composition is HGF. The label on the container indicates that the composition is used for enhancing angiogenesis, and may also indicate directions for in vivo use, such as those described above.

The kit of the invention comprises the container described above and a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The invention will be more fully understood by reference to the following examples. They should not, however, be construed as limiting the scope of the invention. All reference citations herein are incorporated by reference.

EXAMPLE

Recombinant human HGF ("rhuHGF") was produced in CHO cells using a procedure modified from Naka et al., *J. Biol. Chem.*, 267:20114–20119 (1992). rhuHGF-transfected cells were grown in a 400 L bioreactor in medium containing 2% fetal bovine serum for 8 days. Culture supernatant containing rhuHGF was concentrated and clarified, then conditioned by the addition of solid NaCl to 0.3M. rhuHGF was then purified in a single step using cation exchange chromatography. Conditioned, concentrated culture supernatant was loaded onto a column of S-Sepharose Fast Flow equilibrated in 20 mM Tris, pH 7.5, 0.3M NaCl. After washing out unbound protein, rhuHGF was eluted in a linear gradient from 20 mM Tris, pH 7.5, 0.3M NaCl to 20 mM Tris, pH 7.5, 1.2M NaCl. rhuHGF-containing fractions were pooled based on SDS-PAGE analysis. The S Sepharose Fast Flow pool was concentrated and exchanged into 20 mM Tris, pH 7.5, 0.5M NaCl by gel filtration on Sephadex G25 to a final concentration of about 3–5 mg/ml. A rhuHGF stock solution was then prepared by diluting the rhuHGF in buffer (0.5% bovine serum albumin, 0.05% Tween-20, 0.01% Thimersol in PBS).

The effects of rhuHGF on angiogenesis was tested in a rabbit model of hindlimb ischemia. The rabbit model was designed to simulate ischemia characteristics of patients with severe lower extremity arterial occlusive disease. [Takeshita et al., supra]. The effects of vascular endothelial growth factor ("VEGF") were also tested and compared to rhuHGF. The in vivo experiment was conducted essentially as described in Takeshita et al., supra. One femoral artery was resected in each of 24 New Zealand rabbits. Ten days later (Day 0 of study), baseline measurements of calf blood pressure (BP) index; angiographic score of collateral formation; intravascular Doppler-wire analysis of blood flow; and microsphere-based analysis of muscle perfusion at rest and during stress were performed. The animals exhibited similar baseline measurements.

Each group of animals (8 rabbits/group) then received intra-iliac rhuHGF (500 $\mu$g), recombinant human VEGF ("rhuVEGF") (500 $\mu$g) [prepared as described in Ferrara et al., *Methods Enzym.*, 198:391–404 (1991)], or vehicle (saline plus 0.1% rabbit serum albumin), followed by the same dose intravenously at Days 2 and 4 of the study. At Day 30, all measurements were repeated, and the animals were sacrificed. Total muscle weight of each leg was measured and samples were used for capillary density. The results at Day 30 are shown below in Table 1.

TABLE 1

| Day 30 Data | Vehicle | rhuVEGF | rhuHGF |
|---|---|---|---|
| Angiographic Score | 0.46 ± 0.06 | 0.62 ± 0.04† | 0.78 ± 0.07†§ |
| Capillary Density (/mm2) | 158 ± 12 | 247 ± 18† | 282 ± 15†§ |
| BP index (%) | 51.6 ± 4.5 | 69.8 ± 3.1† | 84.5 ± 1.8†§ |
| Blood flow (ml/min) | 17.9 ± 1.1 | 20.6 ± 1.3* | 23.4 ± 1.2†§ |
| Muscle perfusion (rest, %) | 73.2 ± 6.8 | 88.4 ± 6.6* | 99.2 ± 4.5†§ |
| Muscle perfusion (stress, %) | 36.6 ± 8.8 | 65.7 ± 7.5† | 83.3 ± 6.7†§ |
| Muscle weight (%) | 73.0 ± 2.6 | 87.6 ± 2.8* | 95.9 ± 5.4†§ |

% = % of normal limb;
* = $p < .05$ vs vehicle;
† = $p < .001$ vs vehicle;
§ = $p < .05$ vs VEGF The data showed that HGF enhanced collateral vessel formation and regional perfusion, and prevented atrophy. At similar doses in the study, the HGF exhibited greater efficiency than VEGF.

What is claimed is:

1. A method of enhancing angiogenesis for treatment of vascular insufficiency or limb ischemia secondary to arterial occlusive disease, comprising:

administering to a patient in need of same an amount of hepatocyte growth factor (HGF) effective to stimulate angiogenesis in said patient, wherein said HGF is administered intravenously, intraarterially or via infusion.

2. The method of claim 1, wherein said method of administration is intraarterially.

3. The method of claim 2, wherein said intraarterial administration is upstream of an arterial occlusion.

4. The method of claim 1, wherein said patient is human, and said HGF is human HGF.

5. The method of claim 4, wherein said HGF is recombinant HGF.

6. The method of claim 1, wherein said HGF is recombinant HGF.

7. The method of claim 1, wherein said HGF is administered with a pharmaceutical carrier.

* * * * *